United States Patent [19]
Mukogawa

[11] Patent Number: 5,942,763
[45] Date of Patent: Aug. 24, 1999

[54] APPARATUS AND METHOD FOR IDENTIFYING AN IDENTIFICATION MARK OF A WAFER

[75] Inventor: Yasukazu Mukogawa, Tokyo, Japan

[73] Assignee: Mitsubishi Denki Kabushiki Kaisha, Tokyo, Japan

[21] Appl. No.: 08/925,652

[22] Filed: Sep. 9, 1997

[30] Foreign Application Priority Data

Apr. 11, 1997 [JP] Japan .................................... 9-093675

[51] Int. Cl.$^6$ .................................................. G01N 21/86
[52] U.S. Cl. .................................. 250/559.44; 250/559.4
[58] Field of Search .................................. 250/566, 556, 250/559.4, 559.44; 356/237.5

[56] References Cited

U.S. PATENT DOCUMENTS 5,465,145 11/1995 Nakashige et al. .................. 356/237.5

FOREIGN PATENT DOCUMENTS 7-141461 6/1995 Japan .

Primary Examiner—Que T. Le
Attorney, Agent, or Firm—Oblon, Spivak, McClelland, Maier & Neustadt, P.C.

[57] ABSTRACT

A wafer (1) on which an oxide film (3) is formed is disposed on a wafer stage (2), and the surface of the oxide film (3) is irradiated with a laser beam by a laser-beam irradiation unit (4). Then, the laser beam applied to a region having a concave portion (13) is scattered in the surface of the oxide film (3) due to the level difference of the concave portion (13). Accordingly, through a scanning with the laser beam, the scattered light due to the concave portion (13) is received by a scattered-light receptor (5). Subsequently, information on distribution of the scattered light received by the scattered-light receptor (5) is converted into a potential and an OCR process is performed on the potential distribution by an OCR process unit (6), to read the configuration of the concave portion (13) formed in the surface of the oxide film (3) as character information. With this structure, provided is a wafer identification apparatus which is capable of reading an engraved mark on the surface of the wafer with reliability, even if the oxide film and the like is formed on the wafer.

13 Claims, 6 Drawing Sheets

APPARATUS AND METHOD FOR IDENTIFYING AN IDENTIFICATION MARK OF A WAFER

BACKGROUND OF THE INVENTION

1. Field of the Invention

The present invention relates to an apparatus and a method for identifying a wafer.

2. Description of the Background Art

When production control and data control of a semiconductor device are exercised by wafer or lot, it is necessary to identify a wafer that is the foundation of a semiconductor device. In general, for identification of a wafer, lot No. and wafer No. as identification mark are engraved on the surface of the wafer by e.g., a laser.

In the background art, first, the lot No. and the wafer No. engraved on the surface of the wafer are read as graphic information by direct observation of the engraved portion with a CCD camera and secondly a process for recognizing the graphic information as character information (referred to as "OCR process" hereinafter) is performed, to identify the wafer.

FIG. 9 is a partial cross section showing a wafer which is engraved with the lot No. and wafer No. as identification mark on its surface by using a laser. As shown in this figure, engraved portions 7 are formed at the depth of e.g., about 0.2 μm from the surface of a wafer 1. When the lot No. or the like is engraved at the depth of about 0.2 μm or more from the surface of the wafer 1, the engraved mark can be read direct with the CCD camera.

FIG. 10 is a partial cross section showing the wafer 1 and an oxide film 3 formed on the surface of the wafer 1 of FIG. 9. In many cases, the oxide film 3 or the like is formed on the wafer 1 in a process for manufacturing a semiconductor device, where a concave portion 13 is produced in a region of the surface of the oxide film 3 above the engraved portion 7 due to the level difference of the engraved portion 7 and no concave portion is produced in other region.

FIG. 11 is a cross section showing an exemplary wafer identification apparatus in the background art. A light irradiation unit 8 irradiates the surface of the wafer 1 provided with the engraved portion 7 with a light from diagonally above the engraved portion 7. On the other hand, a CCD camera 10 is disposed so that its light-receptive axis should be out of the direction of a regularly-reflected light La, and receives only a reflected light Lb that is reflected on the engraved portion 7. Setting the light-receptive axis of the CCD camera 10 out of the direction of the regularly-reflected light La provides more intense contrast between the engraved portion 7 and the peripheral portion, to offer higher reading performance than simple read of the content of the engraved portion 7 with the CCD camera 10 without light irradiation.

Even if the engraved portion 7 is formed at the depth of about 0.2 μm from the surface of the wafer 1, however, the concave portion 13 is shallower when the oxide film 3 is formed on the surface of the wafer 1 as shown in FIG. 10, and sufficient contrast can not be obtained between the concave portion 13 and its peripheral portion by using the wafer identification apparatus of FIG. 11, as well as by direct read of the surface configuration of the concave portion 13 direct with the CCD camera 10. As a result, the wafer can not be identified.

Considering that the concave portion 13 is shallower than the engraved portion 7 when the oxide film 3 is formed on the surface of the wafer 1, it may be proposed that the engraved portion 7 should be formed deeper from the surface of the wafer 1. But it is impossible to form the engraved portion 7 unlimitedly deeper because more dust would be generated in forming the engraved portion 7, causing deposition of the dust on the surface of the wafer 1 or chemical agents used in the process for manufacturing the semiconductor device would be collected in the engraved portion 7.

SUMMARY OF THE INVENTION

The present invention is directed to a wafer identification apparatus. According to a first aspect of the present invention, the wafer identification apparatus comprises: a light irradiating unit for irradiating a surface of a wafer provided with an identification mark having a level difference with a light; and a light receiving unit for reading the identification mark by receiving a scattered light that is the light scattered from the surface.

According to a second aspect of the present invention, in the wafer identification apparatus of the first aspect, the light is a laser beam.

According to a third aspect of the present invention, the wafer identification apparatus of the second aspect further comprises: at least one filter disposed on an optical axis of the laser beam between the light irradiating unit and the surface, for attenuating the intensity of the laser beam; and at least one filter removing means for removing the at least one filter.

The present invention is also directed to a wafer identification method. According to a fourth aspect of the present invention, the wafer identification method comprises the steps of: (a) scanning a surface of a wafer provided with an identification mark having a level difference with a laser beam; and (b) receiving a scattered light of the laser beam from the surface.

According to a fifth aspect of the present invention, the wafer identification method comprises the steps of: (a) irradiating a surface of a wafer provided with an identification mark having a level difference with a light; (b) projecting a pattern of a reflected light that is the light reflected on the surface on a light receiving surface; and (c) recognizing the pattern on the light receiving surface.

According to a sixth aspect of the present invention, the wafer identification method of the fourth or fifth aspect further comprises the step of: (d) receiving the reflected light direct from the surface before the step (a). In the wafer identification method of the sixth aspect, the step (a) is started only when the identification mark is not read through the step (d).

According to an seventh aspect of the present invention, in the wafer identification method of the fourth aspect, the steps (a) and (b) are repeated until the identification mark is read.

The light applied to the surface of the wafer by the light irradiating unit is scattered only against the identification mark having the level difference in the surface of the wafer. The wafer identification apparatus of the first aspect can read the identification mark, even if it can not read by receiving the reflected light direct with CCD camera because of its shallow level difference, to identify the wafer.

The laser beam is remarkably scattered against the level difference because of high coherence. Therefore, the wafer identification apparatus of the second preferred embodiment can easily read the identification mark by the scattered light.

The wafer identification apparatus of the third aspect allows enhancement of the intensity of the laser beam that is applied to the surface of the wafer while keeping the intensity of the laser beam emitted from the light irradiating unit constant through removing the filter by the filter removing system.

The light applied to the surface of the wafer is scattered only against the identification mark having the level difference in the surface of the wafer. By the wafer identification method of the fourth aspect, the identification mark can be read, even if it can not be read by receiving the reflected light direct with the CCD camera because of its shallow level difference, and therefore the wafer can be identified.

In the wafer identification method of the fifth aspect, the pattern of the reflected light from the surface of the wafer is projected on the light receiving surface and the light reflected on the concave portion of level difference is condensed due to the concavity, to be more brightly shown than other region. Therefore, the pattern of the reflected light on the light receiving surface is easily recognized, and thus the wafer can be identified through easy read of the identification mark.

In the wafer identification method of the sixth aspect, if the identification mark in the surface of the wafer is shown up much clearly against other portion, the reflected light from the surface of the wafer is received direct and thereby the identification mark can be read and if not, the step (a) is started to read the identification mark. That avoids needlessly longer operation time due to performance of the step (a) and the followings if the identification mark is shown up so clearly that it can be read by direct reception of the reflected light, aside from the identification mark that is not shown up so clearly in the surface of the wafer.

In the method identification apparatus of the seventh aspect, the steps (a) and (b) are repeated until the identification mark on the surface of the wafer is read. Specifically, through enhancement of the detecting sensitivity for the scattered light by repeating the scanning with the laser beam more than one time, the identification mark can be read, even if it can not be read by one scanning, and therefore the wafer is identified.

An object of the present invention is to provide an apparatus and a method for identifying a wafer by which an engraved mark formed at such a depth as not to increase dust or collect chemical agents can be read with reliability, even if an oxide film is formed on the surface of a wafer.

These and other objects, features, aspects and advantages of the present invention will become more apparent from the following detailed description of the present invention when taken in conjunction with the accompanying drawings.

DESCRIPTION OF THE PREFERRED EMBODIMENTS

The First Preferred Embodiment

Figure 1:
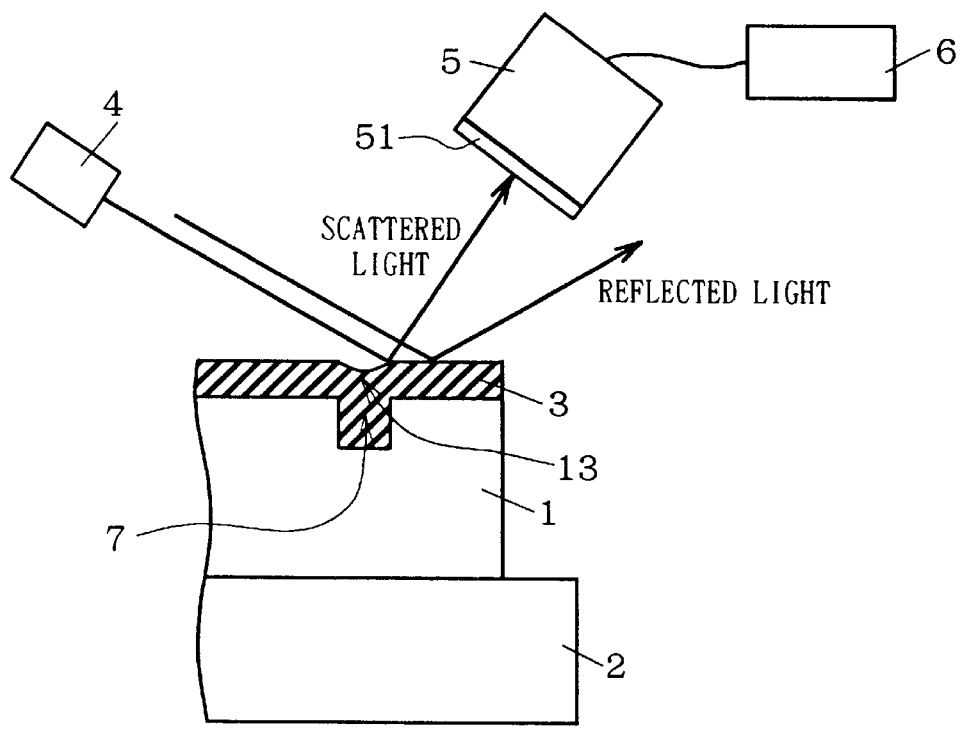
FIG. 1 is a cross section showing a structure of a wafer identification apparatus in accordance with a first preferred embodiment of the present invention.

FIG. 1 is a cross section showing a structure of a wafer identification apparatus in accordance with the first preferred embodiment of the present invention. As shown in this figure, the wafer identification apparatus of the first preferred embodiment comprises a wafer stage 2, a laser-beam irradiation unit 4, a scattered-light receptor 5 having a photoreceptor surface 51 and an OCR process unit 6. On the surface of the wafer 1 disposed on the wafer stage 2, the lot No. and the wafer No. as identification mark are engraved, forming the engraved portion 7. Furthermore, the oxide film 3 is formed on the surface of the wafer 1 on the side of the engraved portion 7, and the concave portion 13 in the surface of the oxide film 3 may be shallower than $0.2 \mu m$ that is a critical depth where it can be read direct with the CCD camera.

A wafer identification method using the wafer identification apparatus of the first preferred embodiment will be discussed step by step. First, the wafer 1 is disposed on the wafer stage 2 and the surface of the wafer 1 on the side of the engraved portion 7 is irradiated with a laser beam by the laser-beam irradiation unit 4. Then, a laser beam applied to a region not having the engraved portion 7 is regularly reflected on the surface of the wafer 1 or the oxide film 3, going as a reflected light of FIG. 1 and another laser beam applied to a region having the engraved portion 7 is scattered due to the level difference of the engraved portion 7 or the concave portion 13, going as a scattered light of FIG. 1. Accordingly, by sequentially moving the laser-beam irradiation unit 4 with the wafer 1 fixed or sequentially moving the wafer 1 together with the wafer stage 2 with the laserbeam irradiation unit 4 fixed, i.e., by scanning the wafer 1 with the laser-beam irradiation, the scattered light due to the engraved portion 7 or the concave portion 13 can be received through the photoreceptor surface 51 of the scattered-light receptor 5.

Next, the information on distribution of the scattered light that is received through the photoreceptor surface 51 is converted into a potential. That provides two-dimensional potential distribution in accordance with the distribution of scattered light. Subsequently, an OCR process is performed on the potential distribution by the OCR process unit 6 to read the configuration of the engraved portion 7 or the concave portion 13 as character information.

Thus, the wafer identification apparatus of the first preferred embodiment can read the configuration of the engraved portion 7 or the concave portion 13 that can not be read by direct light-reception with the CCD camera, to identify the wafer.

Moreover, since the wafer identification method of the first preferred embodiment includes the process for converting the information on the distribution of scattered light into a potential, the potential difference can be amplified by the scattered-light receptor 5. Therefore, this method can read the engraved mark more easily than observation of the engraved portion 7 by direct light-reception with the CCD camera.

The Second Preferred Embodiment

Figure 2:
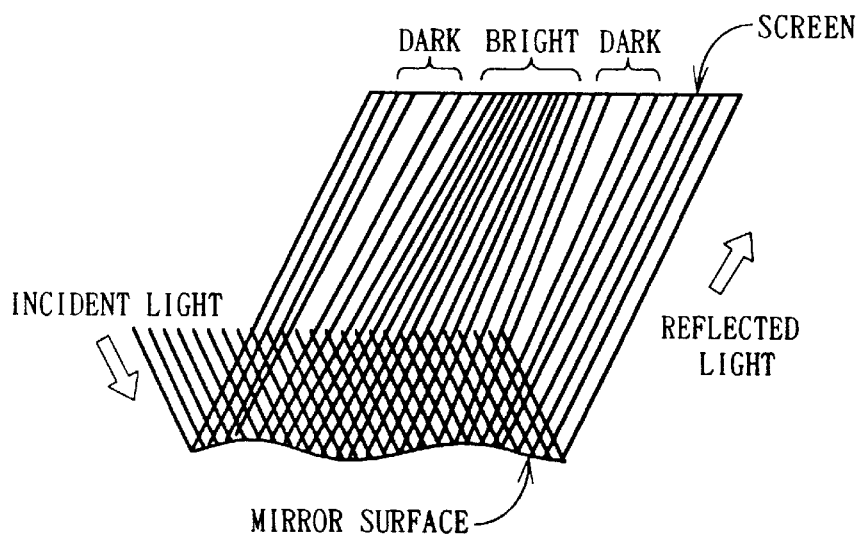
FIG. 2 is a cross section illustrating the principle of magic mirror.

Prior to discussion on the second preferred embodiment, a principle for recognition of unevenness (concave and convex) on a mirror surface (principle of magic mirror) will be described. FIG. 2 is a cross section illustrating the principle of magic mirror. An incident light is given to a mirror surface with unevenness by irradiation from a side. The incident light is reflected on the mirror surface and the reflected light is projected on a screen. The light reflected on a concave portion of the mirror surface is condensed, due to the concavity, to be more brightly shown on the screen, and on the other hand the light reflected on a convex portion of the mirror surface is diverged to be more darkly shown on the screen. Therefore, observation of the difference in brightness of the reflected light on the screen makes the evenness of the mirror surface visible, allowing recognition of the concave and convex on the mirror surface.

Figure 3:
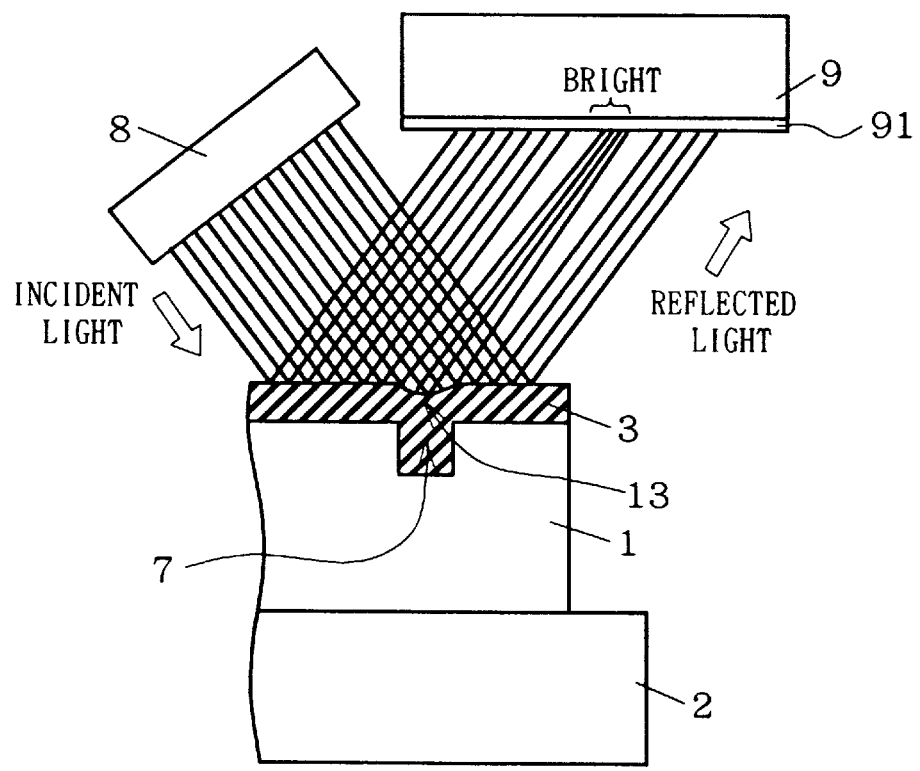
FIGS. 3 and 4 are cross sections each showing a structure of a wafer identification apparatus in accordance with a second preferred embodiment of the present invention.

The second preferred embodiment is a wafer identification apparatus to which the principle of magic mirror applies. A structure of the wafer identification apparatus of the second preferred embodiment is shown in the cross sections of FIGS. 3 and 4. As shown in these figures, the wafer identification apparatus of the second preferred embodiment comprises the wafer stage 2, the light irradiation unit 8, a reflected-light receptor 9 having a photoreceptor surface 91, and the CCD camera 10 and the OCR process unit 6. Like the first preferred embodiment, the engraved portion 7 is formed on the surface of the wafer 1 disposed on the wafer stage 2. Furthermore, the oxide film 3 may be formed on the surface of the wafer 1 on the side of the engraved portion 7, and in this case, the concave portion 13 is formed on the surface of the oxide film 3.

A wafer identification method using the wafer identification apparatus of the second preferred embodiment will be discussed. First, the wafer 1 is disposed on the wafer stage 2 and the surface of the wafer 1 on the side of the engraved portion 7 is irradiated with a light by the light irradiation unit 8 from a side. The reflected light is projected on the photoreceptor surface 91 of the reflected-light receptor 9 (see FIG. 3). According to the principle of magic mirror, the configuration of the engraved portion 7 or the concave portion 13 is shown on the reflected-light receptor 9 with contrast in brightness due to the concavity of the engraved portion 7 or the concave portion 13.

Figure 4:
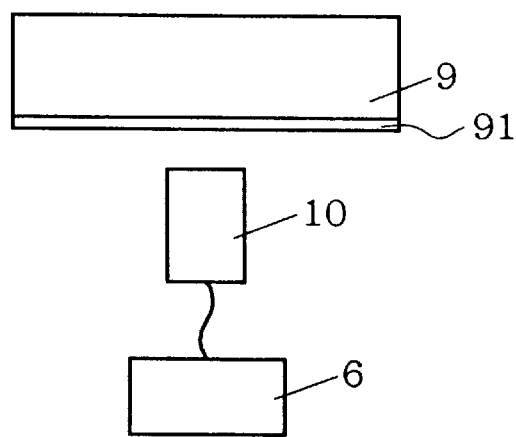

The information shown in the photoreceptor surface 91 about the configuration of the engraved portion 7 or the concave portion 13 is captured by the CCD camera 10 and an OCR process is performed on the information by the OCR process unit 6 (see. FIG. 4). The configuration of the engraved portion 7 or the concave portion 13 is thereby recognized as character information.

Thus, the wafer identification apparatus of the second preferred embodiment can read the configuration of the engraved portion 7 or the concave portion 13 that can not be read by direct light-reception with the CCD camera, to identify a wafer.

The Third Preferred Embodiment

Using the wafer identification apparatus of the first or second preferred embodiment makes it possible to read the configuration of the engraved portion 7 or the concave portion 13 that is too shallow to recognize by direct light-reception with the CCD camera. It takes longer time, however, to identify the wafer than direct read of the configuration of the engraved portion 7 or the concave portion 13 with the CCD camera because of additional processes of irradiating the laser or light and obtaining the difference in brightness of the scattered light or reflected light. For this reason, it is desirable to apply the techniques in accordance with the first and second preferred embodiments only when the configuration can not be read by direct light-reception with the CCD camera.

Figure 5:
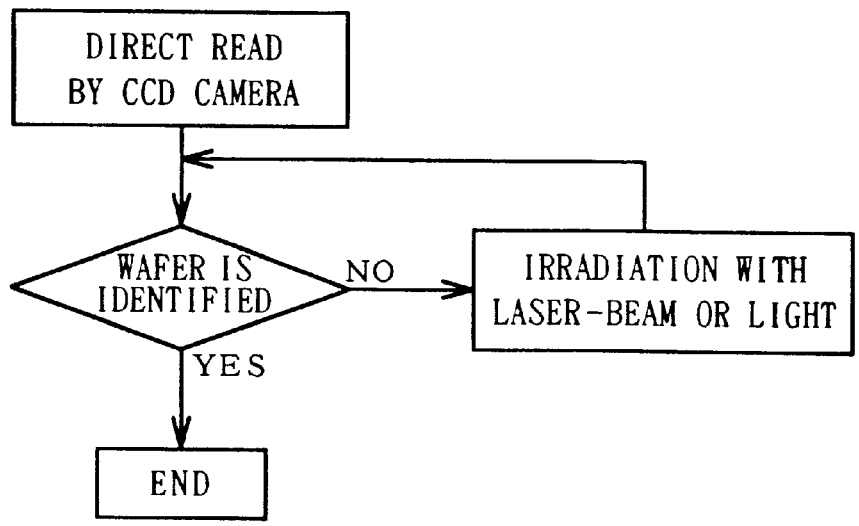
FIG. 5 is a flow chart showing a measuring sequence of a wafer identification method in accordance with a third preferred embodiment of the present invention.

A measuring sequence of a wafer identification method of the third preferred embodiment is shown in the flow chart of FIG. 5. In the first stage, the configuration of the engraved portion 7 or the concave portion 13 is read direct by using the CCD camera in an attempt to identify the wafer. Specifically, direct reception of the light reflected on the engraved portion 7 or the concave portion 13 is performed to read the identification mark. If the wafer is identified in the first stage, the process is completed, and if not, the wafer is identified by using the wafer identification apparatus of the first or second preferred embodiment.

Thus, in the wafer identification method of the third preferred embodiment, the wafer identification apparatus of the first or second preferred embodiment is used only when the wafer can not be identified by direct light-reception with CCD camera. In other words, it is not necessary to use the wafer identification apparatus of the first or second preferred embodiment for the engraved portion or concave portion which is deep enough to recognize by direct read with the CCD camera. Thus, the third preferred embodiment avoids needlessly-prolonged processing time for identification of wafer.

The Fourth Preferred Embodiment

In using the wafer identification apparatus of the first preferred embodiment, if the scattered light is weak in intensity, there may be a case where the scattered-light receptor 5 can not receive enough scattered light to read the configuration of the engraved portion 7 or the concave portion 13. A wafer identification method of the fourth preferred embodiment is intended to increase the detecting sensitivity of the scattered-light receptor 5 step by step, repeating the measurement until the wafer can be identified.

Figure 6:
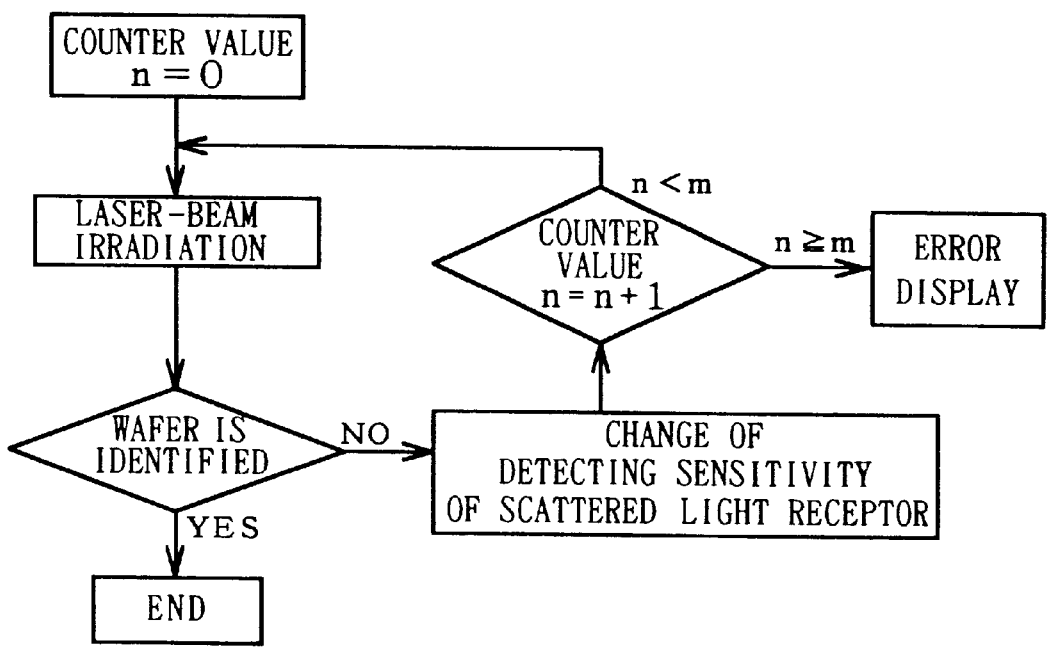
FIG. 6 is a flow chart showing a measuring sequence of a wafer identification method in accordance with a fourth preferred embodiment of the present invention.

A measuring sequence of a wafer identification method of the fourth preferred embodiment is shown in the flow chart of FIG. 6. In the first stage (counter value n=0), the scanning is performed with the laser beam to recognize the identification mark on the wafer, i.e., identify the wafer, in accordance with the method of the first preferred embodiment. If the wafer can be identified in the first stage, the process is completed, and if not, the detecting sensitivity of the scattered-light receptor 5 is enhanced. Specifically discussing, a photomultiplier is used as the scattered-light receptor 5 and the image information captured by the photomultiplier in the first stage is stored. In the second stage (counter value n=1), the scanning is performed with the laser beam in the same manner and the image information captured in the second stage is overlaid on that captured in the first stage. If the wafer can be identified in the second stage, the process is completed, and if not, the same operation as above is repeated until the wafer is identified. The image information overlaid in sequence is easier to read than the individual image information captured in each stage.

Furthermore, the counter value n indicating the number of changes of the detecting sensitivity is stored, and if the counter value n is larger than a predetermined number m, i.e., if $n \geq m$, "ERROR" may be indicated in accordance with judgment that the wafer can not be identified.

Thus, even if the wafer identification apparatus of the first preferred embodiment can not identify a wafer, the wafer identification method of the fourth preferred embodiment allows automatically enhancement in detecting sensitivity of the scattered-light receptor 5 to identify the wafer with higher reliability.

The Fifth Preferred Embodiment

As mentioned earlier, in using the wafer identification apparatus of the first preferred embodiment, if the scattered light is weak in intensity, there may be a case where the scattered-light receptor 5 can not receive enough scattered light to identify the wafer. Though enhancing the detecting sensitivity of the scattered-light receptor 5 makes it possible to identify the wafer as discussed in the fourth preferred embodiment, a method of enhancing the intensity of the laser beam irradiated from the laser-beam irradiation unit 4 may be used to identify the wafer when it is impossible to change the detecting sensitivity of the scattered-light receptor 5 on hardware grounds and the like.

In this case, though the intensity of the scattered light increases as the intensity of the laser beam irradiated from the laser-beam irradiation unit 4 increases, there may be a case where the intensity of the reflected light also increases if the intensity of the laser beam is too high and that makes it hard for the scattered-light receptor 5 to receive the scattered light, being obstructed by the too intense reflected light. For this reason, it is advantageous to achieve identification of wafer by irradiation with a laser beam as weak as possible. Therefore, it is desirable to start with a weak laser beam and enhance the intensity of the laser beam step by step, instead of starting with an intense laser beam.

Figure 7:
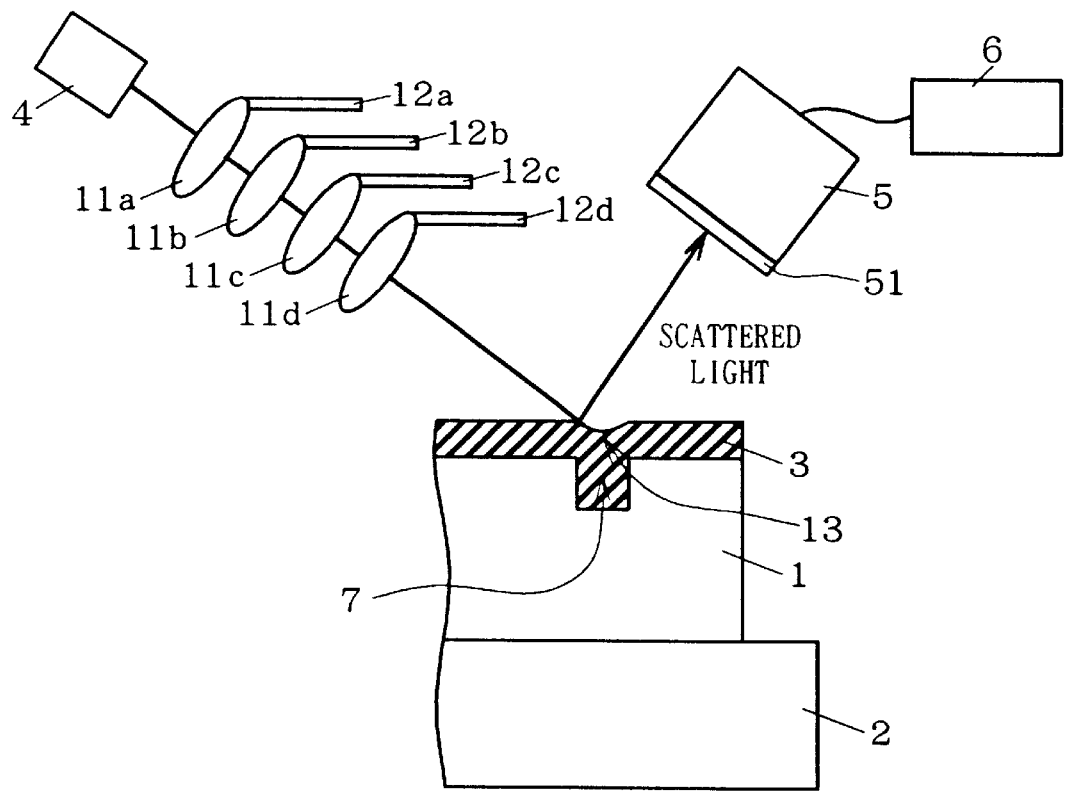
FIG. 7 is a cross section showing a structure of a wafer identification apparatus in accordance with a fifth preferred embodiment of the present invention.

The wafer identification apparatus of the fifth preferred embodiment is intended to implement that. A structure of the wafer identification apparatus of the fifth preferred embodiment is shown in the cross section of FIG. 7. As can be seen from FIG. 7, the wafer identification apparatus of the fifth preferred embodiment is based on that of the first preferred embodiment, and additionally comprises a plurality of filters 11a to 11d disposed on the optical axis of the laser beam between the laser-beam irradiation unit 4 and the surface of the oxide film 3 to attenuate the intensity of the laser beam, and filter removing systems 12a to 12d to remove the filters 11a to 11d respectively. The laser-beam irradiation unit 4 irradiates a laser beam which is maximized in intensity to such an extent that the reflected light should not ill affect the reception of the scattered light.

Figure 8:
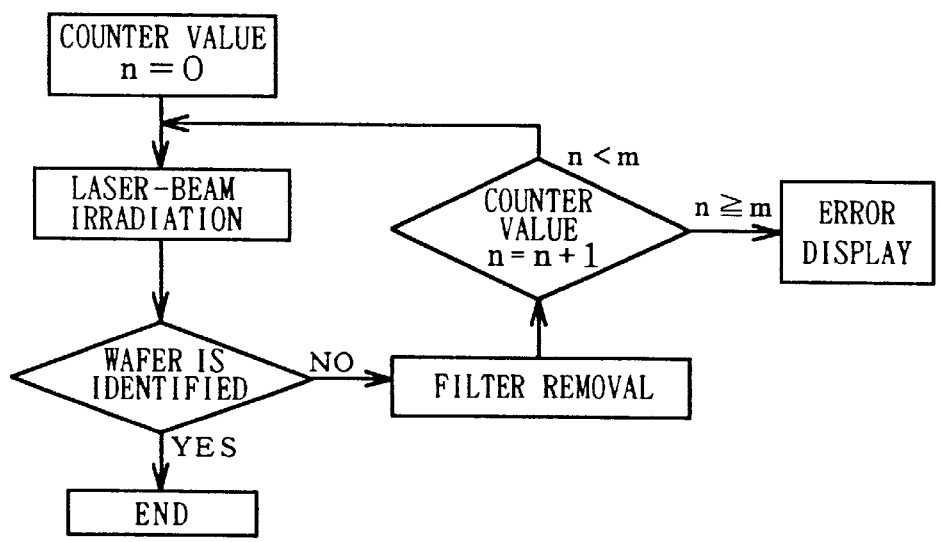
FIG. 8 is a flow chart showing a measuring sequence of a wafer identification method in accordance with the fifth preferred embodiment of the present invention.
Figure 9:
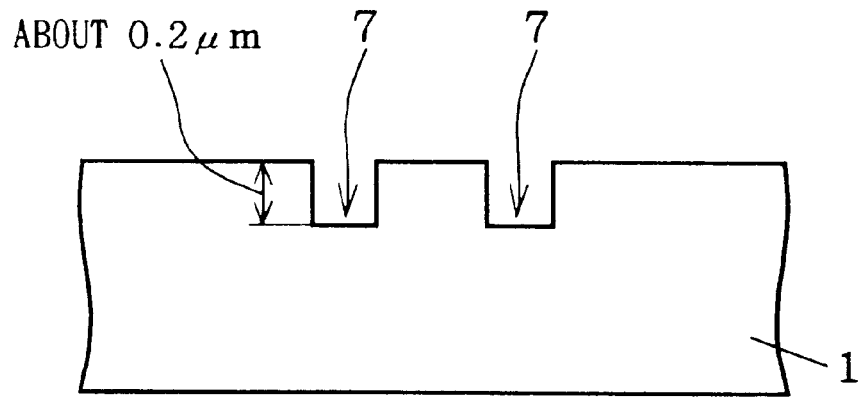
FIG. 9 is a cross section showing a wafer with engraved portions which are formed on its surface by a laser.
Figure 10:
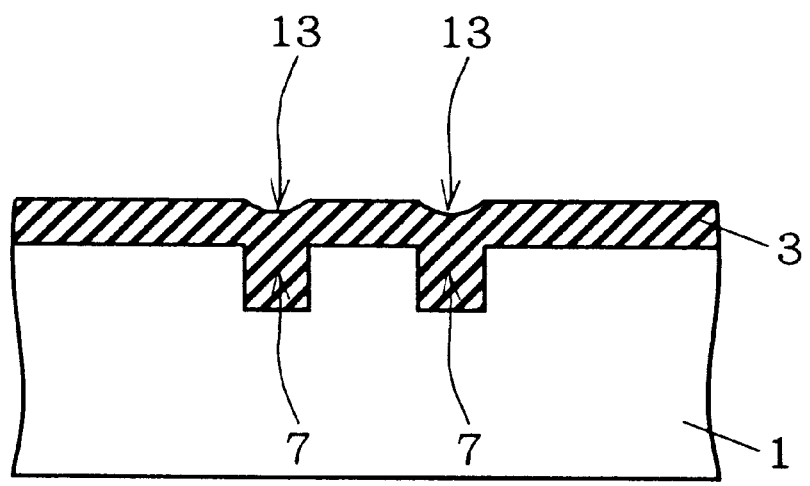
FIG. 10 is a cross section showing a wafer and an oxide film formed on the wafer.
Figure 11:
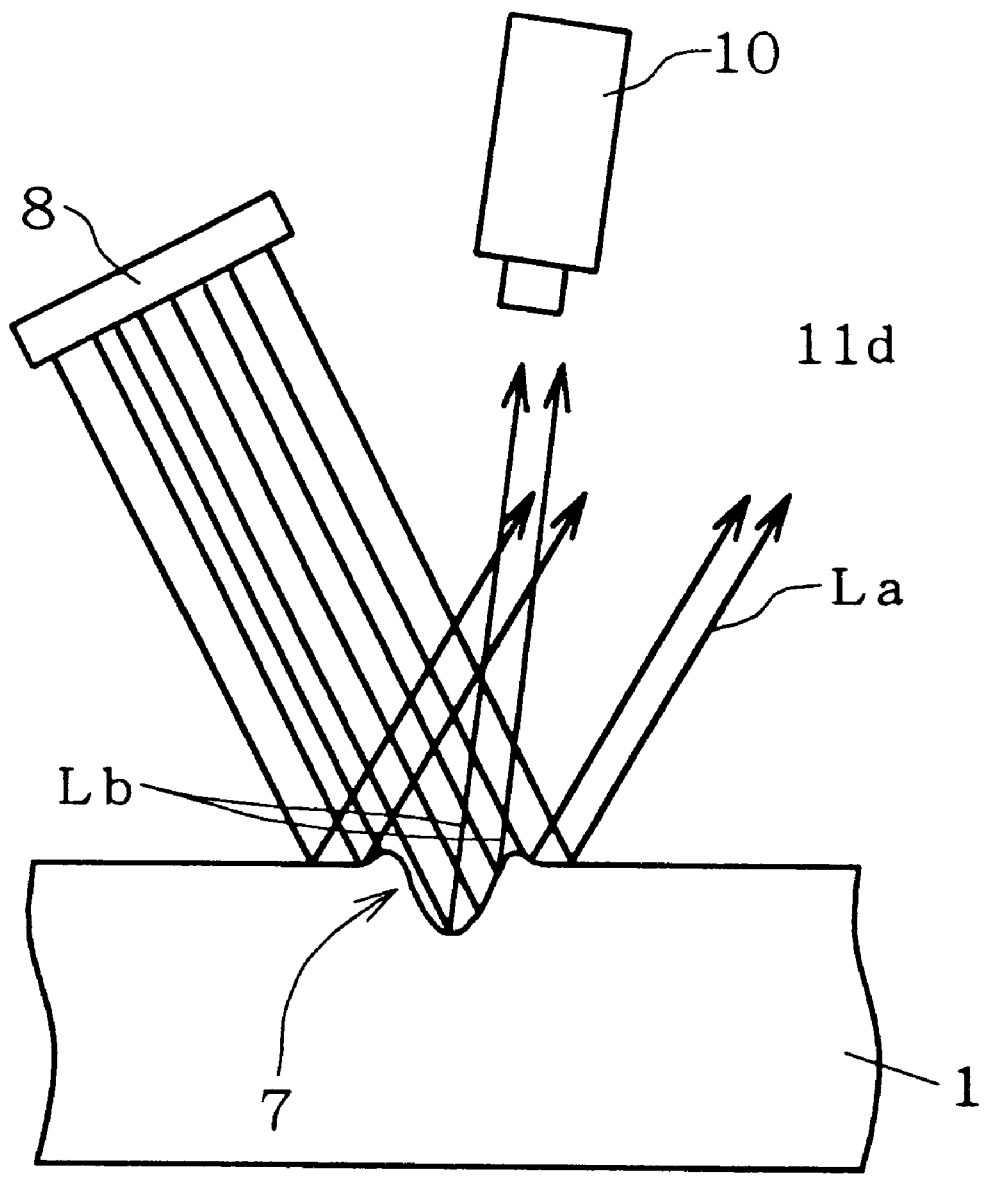
FIG. 11 is a cross section showing an exemplary wafer identification apparatus in the background art.

A measuring sequence of a wafer identification method of the fifth preferred embodiment is shown in the flow chart of FIG. 8. First, under the condition that all the filters 11a to 11d are interposed, in other words, with the laser beam of lowest intensity, the surface of the oxide film 3 is irradiated in an attempt to identify the wafer (counter value n=0). In this stage, if the wafer is identified, the process is completed, and if not, the filter 11a is removed by the filter removing system 12a to enhance the intensity of the laser beam applied to the surface of the oxide film 3 in an attempt to identify the wafer (counter value n=1). If the wafer is not also identified in this stage, the filter 11b is removed by the filter removing system 12b to further enhance the intensity of the laser beam applied to the surface of the oxide film 3 in an attempt to identify the wafer (counter value n=2). The above operation is repeated until the wafer is identified.

Furthermore, the counter value n indicating the number of removed filters is stored, and if the counter value n comes to the number m of initially-interposed filters, i.e., if n=m, "ERROR" is indicated in accordance with judgment that the wafer can not be identified.

Thus, in the wafer identification method using the wafer identification apparatus of the fifth preferred embodiment, the intensity of the laser beam applied to the surface of the oxide film 3 is initially attenuated by the filters 11a to 11d and if the wafer can not be identified, the filters 11a to 11d are automatically removed one by one, by the filter removing systems 12a to 12d. The laser beam is intensified step by step to such an extent that the reflected light should not ill affect the reception of the scattered light, and the wafer can be identified with higher reliability by automatically enhancing the intensity of the laser beam even if the wafer can not be identified by using the wafer identification apparatus of the first preferred embodiment.

While the invention has been shown and described in detail, the foregoing description is in all aspects illustrative and not restrictive. It is therefore understood that numerous modifications and variations can be devised without departing from the scope of the invention.

I claim:

1. A wafer identification apparatus, comprising:

a light irradiating unit for irradiating with a laser beam a surface of a wafer provided with an identification mark, said mark having a bottom surface at a different level than said surface of said wafer; and a light receiving unit for reading said identification mark by receiving light that is scattered from said surface.

2. The wafer identification apparatus of claim 1, further comprising:

at least one filter disposed on an optical axis of said laser beam between said light irradiating unit and said surface, for attenuating the intensity of said laser beam; and at least one filter removing means for removing said at least one filter.

3. The wafer identification apparatus of claim 2, wherein said at least one filter removing means includes a plurality of filter removing means.

4. The wafer identification apparatus of claim 1, wherein said light receiving unit has a light receiving surface for receiving said scattered light to obtain information on distribution of said scattered light.

5. The wafer identification apparatus of claim 4, wherein said light receiving unit further has a photoelectric conversion unit for converting said information on distribution of said scattered light into a potential distribution.

6. The wafer identification apparatus of claim 5, wherein said light receiving unit further has an OCR process unit for reading said potential distribution as character information.

7. A wafer identification method, comprising the steps of:

(a) scanning a surface of a wafer provided with an identification mark with a laser beam said mark having a bottom surface at a different level than said surface of said wafer;

(b) receiving scattered light of said laser beam from said surface.

8. The wafer identification method of claim 7, wherein said steps (a) and (b) are performed while enhancing the intensity of said laser beam step by step.

9. The wafer identification method of claim 7, further comprising the step of:

(d) receiving a reflected light directly from said surface before said step (a), wherein said step (a) is started only when said identification mark is not read through said step (d).

10. The wafer identification method of claim 7, wherein said steps (a) and (b) are repeated until said identification mark is read.

11. The wafer identification method of claim 10, wherein said steps (a) and (b) are stopped when the number of performances exceeds a predetermined number.

12. A wafer identification method, comprising the steps of:
   (a) irradiating a surface of a wafer provided with an identification mark with a light, said mark having a bottom surface at a different level than said surface of said wafer;
   (b) projecting a pattern of reflected light that is reflected from said surface on a light receiving surface; and
   (c) recognizing said pattern on said light receiving surface.

13. The wafer identification method of claim 12, further comprising the step of:
   (d) receiving said reflected light directly from said surface before said step (a),
   wherein said step (a) is started only when said identification mark is not read through said step (d).

* * * * *